United States Patent [19]

Elbe et al.

[11] Patent Number: 4,713,456
[45] Date of Patent: Dec. 15, 1987

[54] PROCESS FOR THE PREPARATION OF 5-ACYLPYRIMIDINES

[75] Inventors: Hans-Ludwig Elbe; Graham Holmwood, both of Wuppertal, Fed. Rep. of Germany

[73] Assignee: Bayer Aktiengesellschaft, Leverkusen, Fed. Rep. of Germany

[21] Appl. No.: 769,639

[22] Filed: Aug. 26, 1985

[30] Foreign Application Priority Data

Aug. 29, 1984 [DE] Fed. Rep. of Germany ....... 3431689

[51] Int. Cl.$^4$ ............... C07D 239/26; C07D 401/06; C07D 403/06; C07D 405/06; C07D 407/06; C07D 409/06; C07D 411/06; C07D 413/06
[52] U.S. Cl. .................................. 544/335; 544/122; 544/2; 544/3; 544/5; 544/8; 544/54; 544/58.4; 544/58.5; 544/63; 544/65; 544/66; 544/67; 544/96; 544/98; 544/180; 544/182; 544/216; 544/238; 544/295; 544/296; 544/162; 544/175; 544/177; 544/398; 544/399; 546/332; 546/334; 546/339; 546/346; 548/566; 548/571; 548/574
[58] Field of Search ............... 544/335, 296, 295, 238, 544/182, 180, 98, 96, 67, 66, 65, 63, 58.5, 58.4, 54, 8, 5, 3, 2, 122, 216

[56] References Cited
U.S. PATENT DOCUMENTS 3,316,267 4/1967 Shen .................................... 544/357

OTHER PUBLICATIONS

Lowe, Chemical Abstracts entry 85:21281n, (1976).
Arnoldi et al., Chemical Abstracts 101:191228s, (1984).
Arnoldi et al., Pestic. Sci., vol. 15, pp. 303–309, (1985).
Acta Chemica Scandinavica, Series B, Organic Chemistry and Biochemistry, vol. B36, No. 8, 1982, pp. 529–531, T. Benneche et al.
Brown, The Pyrimidines, Interscience Pub., 1962, pp. 31–38.
Widmer, Synthesis, Communications, 1983, pp. 135, 136.
Arnold et al, Collect. Czech. Comm., vol. 28, 1963, pp. 869–881.

Primary Examiner—John M. Ford
Attorney, Agent, or Firm—Sprung Horn Kramer & Woods

[57] ABSTRACT

A process for the preparation of a 5-acylpyrimidine of the formula

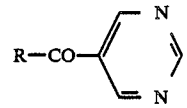

in which R is an organic radical comprising reacting a methyl ketone of the formula

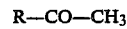

in a first stage with a formylating reagent in the presence of a base to form an enolketone of the formula

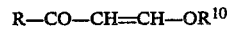

in which $R^{10}$ represents hydrogen or a base radical, thereafter reacting the enolketone in 2nd and 3rd stages with formamidine or a formamidine salt, and with an amino-formylating agent, and, in a 4th stage heating to cyclize the compound formed.

The end products, some of which are new, are intermediates for making herbicides.

3 Claims, No Drawings

PROCESS FOR THE PREPARATION OF 5-ACYLPYRIMIDINES

The present invention relates to a new process for the preparation of 5-acylpyrimidines, some of which are known and which can be used as intermediates for the preparation of substances having a plant growth-regulating and fungicidal activity.

It is already known that pyrimidinylcarbinols can be used as intermediates for the preparation of benzyl pyrimidinyl-alkyl ethers with plant growth-regulating and fungicidal properties (See U.S. Pat. No. 4,436 907 issued Mar. 13, 1984.)

Thus, benzyl pyrimidinyl-alkyl ethers are obtained when pyrimidinylcarbinols are reacted with benzyl halides in accordance with the following equation:

$$R^1-CH_2-Hal + H-O-CH-R^2 \longrightarrow$$

(pyrimidine ring attached)

$$R^1-CH_2-O-CH-R^2 + H\,Hal$$

(pyrimidine ring attached)

$R_1$=optionally substituted phenyl,
$R_2$=alkyl, optionally substituted cycloalkyl or optionally substituted phenyl and
Hal=halogen.

The disadvantage of this known process is, however, that the pyrimidinylcarbinols required as starting substances are producible only with difficulty. Thus, these pyrimidinylcarbinols can be prepared by reacting pyrimidinyl halides with an alkali metal-organic compound, such as, for example, n-butyl-lithium, and then with corresponding aldehydes at low temperatures, for example between $-100°$ and $-120°$ C. (See U.S. Pat. No. 4,436 907 issued Mar. 13, 1984 ) The use of organometallic compounds at such low temperatures makes practical application of this process on an industrial scale virtually impossible.

Another disadvantage of this process is that the price of the pyrimidinyl halide required as a starting substance is extremely high. There is therefore a great interest in a process which allows a more simpler synthesis of the highly active benzyl pyrimidinyl-alkyl ethers of the abovementioned general formula.

It is also known that 5-acetylpyrimidine can be obtained from 5-acetyl-uracil via 2,4-dichloro-5-acetyl-pyrimidine by reductive dehalogenation (compare Arch. Pharm. 299, 362 (1966)). The yield of end product in this multi-stage process is, however, very low.

It is furthermore known that 5-(2-hydroxybenzoyl)-pyrimidine is obtained when chromone-3-carbaldehyde is reacted with formamidine (compare Synthesis 1976, 274). The yield here is also unsatisfactory. In addition, this process variant cannot be generalized for 5-benzoylpyrimidines with any desired substituents in the phenyl part.

It is moreover known that certain substituted 5-acyl-pyrimidines can be obtained if a methyl ketone is formylated, the product is further reacted to give the enol-acetate, the enol-acetate is formylated with ethyl orthoformate and, finally, cyclization to the pyrimidine is carried out with, for example, methylisothiourea (compare Acta Chemica. Scandinavia B 36, 529–31 (1982)). This process has the disadvantage of a multi-stage reaction, in which the intermediates are isolated.

It has now been found that 5-acylpyrimidines of the formula $$R-CO-\underset{N}{\underset{|}{\overset{N}{\diagup}}}\,\,\,\,\,\,\,\,\,\,\,\,(I)$$

in which R represents alkyl, alkenyl, alkinyl, optionally substituted cycloalkyl, optionally substituted cycloalkylalkyl, optionally substituted phenyl, optionally substituted heteroaryl or the groupings $$-\underset{CH_2R^4}{\overset{CH_2R^3}{\underset{|}{\overset{|}{C}}}}-CH_3,\quad -\underset{CH_3}{\overset{CH_3}{\underset{|}{\overset{|}{C}}}}-R^5 \text{ and } -\underset{CH_3}{\overset{CH_3}{\underset{|}{\overset{|}{C}}}}-(CH_2)_n-R^6$$

wherein
$R^3$ represents halogen;
$R^4$ represents hydrogen or halogen;
$R^5$ represents alkenyl, alkinyl or the CHO group and derivatives thereof;
$R^6$ represents cyano, optionally substituted phenyl or the groupings $-XR^7$ and $-CONR^8R^9$,
wherein
$R^7$ represents alkyl, halogenoalkyl, optionally substituted phenyl or optionally substituted phenylalkyl;
$R^8$ represents hydrogen, alkyl or optionally substituted phenyl;
$R^9$ represents hydrogen or alkyl;
X represents oxygen or sulphur and
the index n represents the number 0, 1 or 2,
can be prepared by a process in which methyl ketones of the formula $$R-CO-CH_3 \qquad (II)$$

in which R has the abovementioned meaning,
(a) are reacted in a 1st stage with a formylating reagent in the presence of a base and if appropriate in the presence of a diluent and, if appropriate, the product is acidified, and thereafter, in a 2nd stage, the enol-ketones formed, of the formula $$R-CO-CH=CH-OR^{10} \qquad (III)$$

in which
R has the abovementioned meaning and
$R^{10}$ represents hydrogen or a base radical,
are reacted, with or without intermediate isolation, with formamidine, it being possible for the formamidine optionally to be in the form of a formamidine salt, if appropriate in the presence of a diluent; and subsequently, in a 3rd stage, the formamidine derivatives formed, of the formula $$R-CO-CH_2-CH=N-CH=NH \qquad (IV)$$

in which R has the abovementioned meaning, are reacted, with or without intermediate isolation, with an amino-formylating agent, if appropriate in the presence of a diluent; and, in a 4th stage, the compounds formed, of the formula

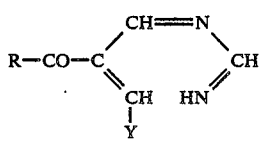
(V)

in which

R has the abovementioned meaning and

Y represents the nitrogen-containing radical of an amino-formylating agent, are cyclized by means of heat, with or without intermediate isolation; or (b) are reacted, in a 1st stage with a formylating reagent in the presence of a base and, if appropriate, in the presence of a diluent, and the product is then acidified, and thereafter, in a 2nd stage, the enol-ketones formed, of the formula

(IIIa)

in which R has the abovementioned meaning, are reacted, with or without intermediate isolation, with an amino-formylating agent, if appropriate in the presence of a diluent, and, in a 3rd stage, the compounds formed, of the formula

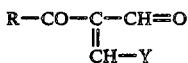
(VI)

in which R and Y have the abovementioned meaning, are reacted, with or without intermediate isolation, with formamidine, if appropriate in the presence of a diluent, and the product is then cyclized by means of heat.

Finally, it has been found that the 5-acylpyrimidines of the formula (I) are particularly suitable as intermediates for the preparation of benzyl pyrimidinyl-alkyl ethers with a plant growth-regulating and fungicidal activity.

The course of the process according to the invention is to be described as extremely surprising both in variant (a) and in variant (b).

Thus, in view of the known prior art, it was to be expected that the intermediate of the formula (IV) formed when carrying out variant (a) (preparation from the formal diketone R—CO—CH$_2$—CHO and formamidine) cyclizes to give the corresponding 4-substituted pyrimidine in accordance with the following equation:

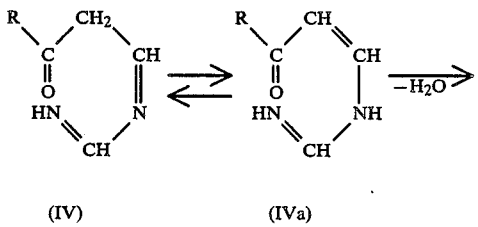

Such cyclizations of β-diketones with amidines to give 4-substituted pyrimidines have frequently been described in the literature (compare, for example, D. J. Brown, The Pyrimidines, page 36, Interscience Publishers, 1962). Surprisingly, however, such a cyclization reaction does not occur in the course of variant (a) of the process according to the invention.

It is also surprising that when carrying out process variant (b), the reaction of the enol-ketone of the formula (IIIa) with a basic amino-formylating agent (compare 2nd stage) to give compounds of the formula (VI) is effected without the acid OH group of the enol-ketone of the formula (IIIa) being alkylated. In fact, it is known from the prior art that acid OH groups can be alkylated with amino-formylating agents (compare Synthesis 1983, 135–136).

Finally, it is also surprising that the intermediate of the formula (VI) can further react as such in the course of the reaction according to process variant (b) without decarbonylation occurring to the expected degree in accordance with the following equation:

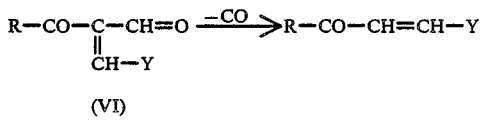

The exceptionally easy decarbonylation of compounds of the type of formula (VI) is known from the literature (compare Collect. Czech. Comm. 28, 869 et seq.). An analogous reaction in the course of variant (b) of the process according to the invention was therefore to be expected.

The process according to the invention is distinguished by a number of advantages. Thus, the desired 5-acylpyrimidines of the formula (I) can be prepared in a simple manner—even on an industrial scale. The yields are relatively high. It is particularly advantageous that none of the intermediates which arise have to be isolated, so that the process is in principle a one-pot process, which means that particularly good space/time yields can be achieved. Moreover, it should be emphasized that the 5-acylpyrimidines of the formula (I) which are accessible by process variants (a) and (b) according to the invention, which differ only in the sequence of the addition of the formylating and amino-formylating agents, can be converted into benzyl pyrimidinyl-alkyl ethers, which have plant growth-regulating and fungicidal properties, by subsequent reduction and reaction of the carbinols thereby formed with benzyl halides. A method for the synthesis of the plant growth-regulating and fungicidal active compounds which is substantially simpler than the processes known hitherto is therefore now available. In addition, in contrast to the previous process, this new process can also be applied on an industrial scale without difficulties.

Only some of the 5-acylpyrimidines which can be prepared by the process according to the invention were known hitherto. The 5-acylpyrimidines of the formula

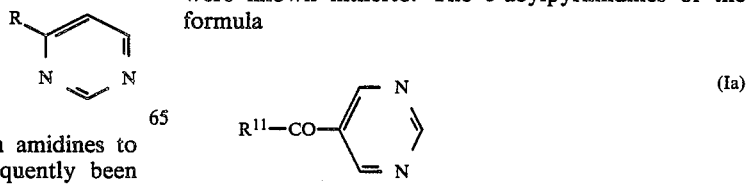
(Ia)

in which $R^{11}$ represents straight-chain alkyl with more than 4 carbon atoms, branched alkyl, alkenyl, alkinyl, optionally substituted cycloalkyl, optionally substituted cycloalkylalkyl, optionally substituted phenyl (with the exception of 2-hydroxyphenyl), optionally substituted heteroaryl and the groupings

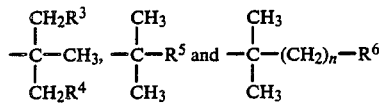

wherein
- $R^3$ represents halogen;
- $R^4$ represents hydrogen or halogen
- $R^5$ represents alkenyl, alkinyl or the CHO group and derivatives thereof;
- $R^6$ represents cyano, optionally substituted phenyl or the groupings $-XR^7$ and $-CONR^8R^9$, wherein
- $R^7$ represents alkyl, halogenoalkyl, optionally substituted phenyl or optionally substituted phenylalkyl;
- $R^8$ represents hydrogen, alkyl or optionally substituted phenyl;
- $R^9$ represents hydrogen or alkyl;
- X represents oxygen or sulphur and
- the index n represents the number 0, 1 or 2, are new.

In the compounds of the formula (Ia) $R^{11}$ preferably represents straight-chain or branched alkyl with 5 to 12 carbon atoms, straight-chain or branched alkenyl with 3 to 6 carbon atoms, straight-chain or branched alkinyl with 3 to 6 carbon atoms or cycloalkyl or cycloalkylalkyl with in each case 3 to 7 carbon atoms in the cycloalkyl part and 1 to 4 carbon atoms in the alkyl part and in each case optionally mono-, di- or tri-substituted by identical or different alkyl substituents with 1 to 4 carbon atoms; or represents phenyl which is optionally mono-, di- or tri-substituted by identical or different substituents, substituents which may be mentioned being: halogen, alkyl, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms, such as fluorine and chlorine atoms; nitro, cyano and alkoxycarbonyl with 1 to 4 carbon atoms in the alkoxy part; and phenyl and phenoxy, in each case optionally substituted by halogen; or furthermore represents 5- to 6-membered heteroaryl which has 1 to 3 hetero-atoms, such as oxygen, nitrogen and/or sulphur, and is optionally mono-, di- or tri-substituted by identical or different substituents, possible substituents being the abovementioned substituents on phenyl, or represents the groupings

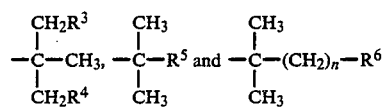

wherein
- $R^3$ preferably represents fluorine, chlorine or bromine;
- $R^4$ preferably represents hydrogen, fluorine, chlorine or bromine;
- $R^5$ preferably represents straight-chain or branched alkenyl with 2 to 4 carbon atoms, straight-chain or branched alkinyl with 3 to 5 carbon atoms, or the CHO group and derivatives thereof, such as oximes, oxime ethers and acetals, for example alkoximinomethyl with 1 to 4 carbon atoms in each alkoxy part, dialkoxymethyl with 1 to 4 carbon atoms in each alkoxy part and optionally substituted dioxolanes and dioxanes;
- $R^6$ preferably represents cyano, or represents phenyl which is optionally mono-, di- or tri-substituted by identical or different substituents, possible substituents being the substituents on phenyl which have already been mentioned above, or represents the groupings $-XR^7$ and $-CONR^8R^9$, wherein
- $R^7$ preferably represents straight-chain or branched alkyl with 1 to 6 carbon atoms or halogenoalkyl with 1 to 4 carbon atoms and 1 to 5 identical or different halogen atoms, such as fluorine and chlorine atoms, or represents phenyl or phenylalkyl, with 1 or 2 carbon atoms in the alkyl part, each of which is optionally mono-, di- or tri-substituted by identical or different substituents, possible substituents in each case being the substituents on phenyl which have already been mentioned above;
- $R^8$ preferably represents hydrogen or straight-chain or branched alkyl with 1 to 4 carbon atoms, or represents phenyl which is optionally mono-, di- or tri-substituted by identical or different substituents, possible substituents being the substituents on phenyl which have already been mentioned above;
- $R^9$ referably represents hydrogen or straight-chain or branched alkyl with 1 to 4 carbon atoms;
- X represents oxygen or sulphur and
- n represents the number 0, 1 or 2.

Particularly preferred compounds of the formula (Ia) are those in which $R^{11}$ represents straight-chain alkyl with 5 to 8 carbon atoms, or represents isopropyl, tert.-butyl, neopentyl, allyl or propargyl, or represents cyclopropyl, cyclobutyl, cyclopentyl or cyclohexyl, each of which is optionally mono- or di-substituted by identical or different substituents from the group comprising methyl, ethyl, isopropyl and tert.-butyl, or represents phenyl which is optionally mono- or di-substituted by identical or different substituents, substituents which may be mentioned being: fluorine, chlorine, methyl, ethyl, isopropyl, tert.-butyl, methoxy, methylthio, trifluoromethyl, trifluoromethoxy, trifluoromethylthio, nitro, cyano and methoxycarbonyl, and phenyl and phenoxy, each of which is optionally substituted by chlorine or fluorine; or furthermore represents furyl, thienyl, benzofuryl, benzothienyl, pyridinyl or pyrimidinyl, each of which is optionally mono- or di-substituted by identical or different substituents, possible substituents being the above-mentioned substituents on phenyl; or represents the groupings

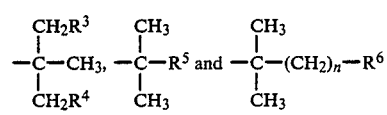

wherein
- $R^3$ represents fluorine or chlorine;
- $R^4$ represents hydrogen, fluorine or chlorine;
- $R^5$ represents vinyl, propargyl, the $-CH=O$ group, methoximinomethyl, dimethoxymethyl or the dioxolane or 1,3-dioxane radical;

R⁶ represents cyano or phenyl which is optionally mono- or di-substituted by identical or different substituents, possible substituents being the substituents on phenyl which have already been mentioned above, or represents the groupings —XR⁷ and —CONR⁸R⁹;

wherein

R⁷ represents straight-chain or branched alkyl with 1 to 4 carbon atoms or halogenoalkyl with 1 or 2 carbon atoms and 1 to 5 identical or different halogen atoms, such as fluorine and chlorine atoms, or represents phenyl or benzyl, each of which is optionally mono- or di-substituted by identical or different substituents, possible substituents in each case being the substituents on phenyl which have already been mentioned above;

R⁸ represents hydrogen, methyl, ethyl, isopropyl or phenyl which is optionally mono- or di-substituted by identical or different substituents, possible substituents being the substituents on phenyl which have already been mentioned above;

R⁹ represents hydrogen, methyl or isopropyl;

X represents oxygen or sulphur and n represents the number 0, 1 or 2.

If, for example, methoxy-tert.-butyl methyl ketone is used as the starting substance, ethyl formate in the presence of sodium methylate is used as the formylating reagent, formamidine is used in the form of the acetate and N,N-dimethylformamide dimethyl acetal is used as the amino-formylating agent, the course of the reaction of the process according to the invention in variant (a) can be represented by the following equation:

1st stage

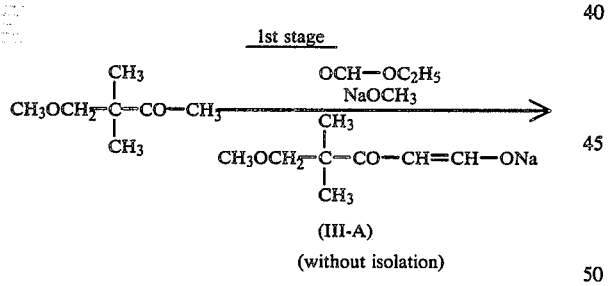

(III-A)
(without isolation)

2nd stage

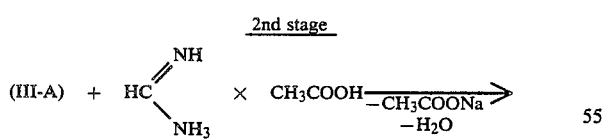

3rd stage

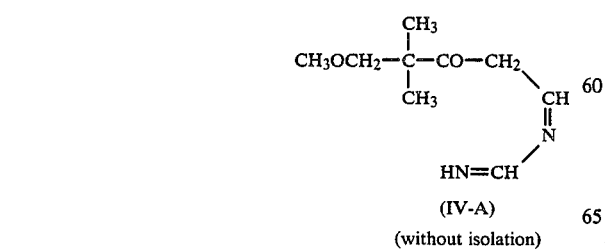

(IV-A)
(without isolation)

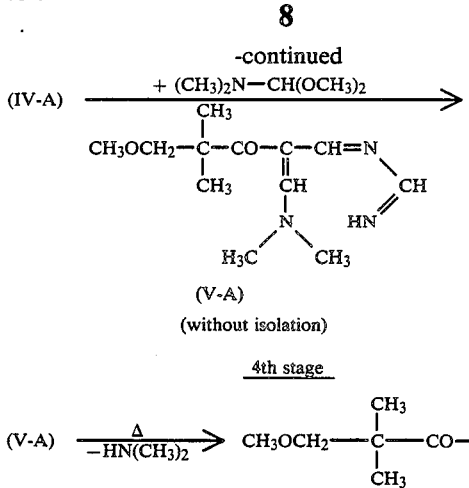

(V-A)
(without isolation)

4th stage (V-A) $\xrightarrow[-HN(CH_3)_2]{\Delta}$

If, for example, 2,4-dichlorophenyl methyl ketone is used as the starting substance, ehtyl formate in the presence of sodium methylate is used as the formylating reagent, N,N-dimethylformamide dimethyl acetal is used as the amino-formylating agent and formamidine is used for the cyclization, the course of the reaction of the process according to the invention in variant (b) can be represented by the following equation:

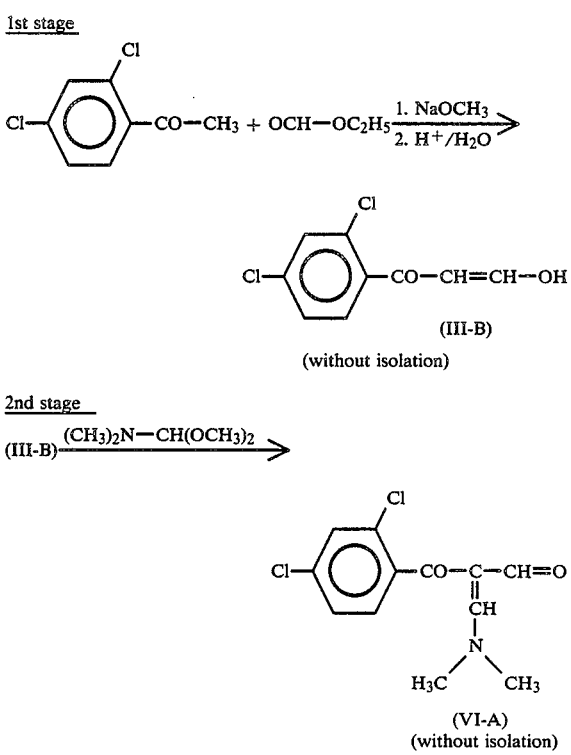

Formula (II) provides a general definition of the methyl ketones required as starting substances in carrying out the process according to the invention. In this formula R preferably represents straight-chain or branched alkyl with 1 to 12 carbon atoms, straight-chain or branched alkenyl with 3 to 6 carbon atoms, straight-chain or branched alkinyl with 3 to 6 carbon atoms or cycloalkyl and cycloalkylalkyl with in each case 3 to 7 carbon atoms in the alkyl part and in each case optionally mono-, di- or tri-substituted by identical or different alkyl substituents with 1 to 4 carbon atoms; or represents phenyl which is optionally mono-, di- or tri-substituted by identical or different substituents, substituents which may be mentioned being: halogen; alkyl, hydroxyl, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms, such as fluorine and chlorine atoms; nitro, cyano and alkoxycarbonyl with 1 to 4 carbon atoms in the alkoxy part, and phenyl and phenoxy, in each case optionally substituted by halogen; or furthermore represents 5- to 6-membered heteroaryl which has 1 to 3 hetero-atoms, such as oxygen, nitrogen and/or sulphur, and is optionally mono-, di- or tri-substituted by identical or different substituents, possible substituents being the abovementioned substituents on phenyl, or represents the groupings

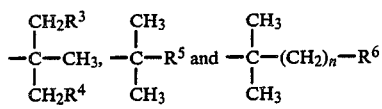

wherein
$R^3$ preferably represents fluorine, chlorine or bromine,
$R^4$ preferably represents hydrogen, fluorine, chlorine or bromine;
$R^5$ preferably represents straight-chain or branched alkenyl with 2 to 4 carbon atoms, straight-chain or branched alkinyl with 3 to 5 carbon atoms, or the CHO group and derivatives thereof, such as oximes, oxime ethers and acetals, for example alkoximinomethyl with 1 to 4 carbon atoms in each alkoxy part, dialkoxymethyl with 1 to 4 carbon atoms in each alkoxy part and optionally substituted dioxolanes and dioxanes;
$R^6$ preferably represents cyano, or represents phenyl which is optionally mono-, di- or tri-substituted by identical or different substituents, possible substituents being the substituents on phenyl which have already been mentioned above, or represents the groupings —$XR^7$ and —$CONR^8R^9$,
wherein
$R^7$ preferably represents straight-chain or branched alkyl with 1 to 6 carbon atoms or halogenoalkyl with 1 to 4 carbon atoms and 1 to 5 identical or different halogen atoms, such as fluorine and chlorine atoms, or represents phenyl or phenylalkyl, with 1 or 2 carbon atoms in the alkyl part, each of which is optionally mono-, di- or tri-substituted by identical or different substituents, possible substituents in each case being the substituents on phenyl which have already been mentioned above;
$R^8$ preferably represents hydrogen or straight-chain or branched alkyl with 1 to 4 carbon atoms, or represents phenyl which is optionally mono-, di- or tri-substituted by identical or different substituents, possible substituents being the substituents on phenyl which have already been mentioned above;
$R^9$ preferably represents hydrogen or straight-chain or branched alkyl with 1 to 4 carbon atoms;
X represents oxygen or sulphur and
n represents the number 0, 1 or 2.

Particularly preferred compounds of the formula (II) are those in which R represents methyl, ethyl, n-propyl, isopropyl, n-butyl, tert.-butyl, n-pentyl, neopentyl, n-hexyl, n-heptyl, n-octyl, allyl or propargyl, or represents cyclopropyl, cyclobutyl, cyclopentyl or cyclohexyl, each of which is optionally mono-or di-substituted by identical or different substituents from the group comprising methyl, ethyl, isopropyl and tert.-butyl, or represents phenyl which is optionally mono- or di-substituted by identical or different substituents, substituents which may be mentioned being: fluorine, chlorine, hydroxyl, methyl, ethyl, isopropyl, tert.-butyl, methoxy, methylthio, trifluoromethyl, trifluoromethoxy, trifluoromethylthio, nitro, cyano and methoxycarbonyl, and phenyl and phenoxy, each of which is optionally substituted by fluorine or chlorine; or furthermore represents furyl, thienyl, benzofuryl, benzothienyl, pyridinyl or pyrimidinyl, each of which is optionally mono- or di-substituted by identical or different substituents, possible substituents being the abovementioned substituents on phenyl; or represents the groupings

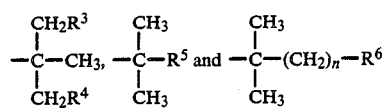

wherein
$R^3$ represents fluorine or chlorine;
$R^4$ represents hydrogen, fluorine or chlorine;
$R^5$ represents vinyl, propargyl, the —CH═O group, methoximinomethyl, dimethoxymethyl or the dioxolane or 1,3-dioxane radical;
$R^6$ represents cyano or phenyl which is optionally mono- or di-substituted by identical or different substituents, possible substituents being the substituents on phenyl which have already been mentioned above, or represents the groupings —$XR^7$ and —$CONR^8R^9$;
wherein
$R^7$ represents straight-chain or branched alkyl with 1 to 4 carbon atoms or halogenoalkyl with 1 or 2 carbon atoms and 1 to 5 identical or different halogen atoms, such as fluorine and chlorine atoms, or represents phenyl or benzyl, each of which is optionally mono- or di-substituted by identical or different substituents, possible substituents in each case being the substituents on phenyl which have already been mentioned above;
$R^8$ represents hydrogen, methyl, ethyl, isopropyl or phenyl which is optionally mono- or di-substituted by identical or different substituents, possible substituents being the substituents on phenyl which have already been mentioned above;
$R^9$ represents hydrogen, methyl or isopropyl;
X represents oxygen or sulphur and
n represents the number 0, 1 or 2.

The methyl ketones of the formula (II) are known or can be prepared in a simple manner by known processes.

Possible formylating agents both for carrying out the first stage of variant (a) and for carrying out the first stage of variant (b) are, preferably, formic acid alkyl esters with 1 to 4 carbon atoms in the alkyl group, or phenyl formate. These formylating agents are generally known compounds of organic chemistry.

The formamidine to be used as a reaction component in carrying out the 2nd stage of variant (a) or in carrying out the 3rd stage of variant (b) can be employed either as such or in the form of a salt with an organic or inorganic acid. Examples of acids which may be mentioned are hydrochloric acid and acetic acid.

Possible amino-formylating agents both for carrying out the 3rd stage of variant (a) and for carrying out the 2nd stage of variant (b) are all the reagents which are customary for such purposes and which are capable of converting an activated methylene group into an enamine. Reagents which can preferably be used are:

(α) formamide acetals of the formula

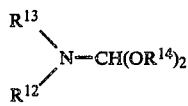  (VII)

in which

R$^{12}$ and R$^{13}$ independently of one another represent alkyl with 1 to 4 carbon atoms or, together with the nitrogen atom to which they are bonded, represent an optionally substituted N-heterocyclic radical and R$^{14}$ represents alkyl with 1 to 4 carbon atoms, (β) aminal esters of the formula

  (VIII)

in which, R$^{12}$, R$^{13}$ and R$^{14}$ have the abovementioned meaning; and (γ) formiminium halides of the formula

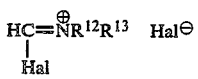  (IX)

in which

R$^{12}$ and R$^{13}$ have the abovementioned meaning and

Hal represents halogen.

In the abovementioned compounds of the formulae (VII), (VIII) and (IX),

R$^{12}$ and R$^{13}$ independently of one another particularly preferably represent methyl, ethyl, n-propyl, isopropyl or n-butyl, or R$^{12}$ and R$^{13}$, together with the nitrogen atom to which they are bonded, particularly preferably represent pyrrolidinyl, piperidinyl, morpholinyl or N-methyl-piperazinyl.

In the compounds of the formulae (VII) and (VIII), R$^{14}$ particularly preferably represents methyl, ethyl or n-propyl.

In the compounds of the formula (IX), Hal particularly preferably represents chlorine or bromine.

The amino-formylating agents of the formulae (VII), (VIII) and (IX) are generally known compounds of organic chemistry.

In the compounds of the formulae (V) and (VI), the meaning of the substituent Y depends on which amino-formylating agent is used. If compounds of the formulae (VII), (VIII) or (IX) are employed, compounds of the formulae (V) or (VI) in which Y represents the grouping of the formula

wherein R$^{12}$ and R$^{13}$ have the abovementioned meanings, are formed.

Preferred possible diluents for all the stages of both process variants are inert, aprotic solvents. These include, preferably, ethers, such as diethyl ether, diisopropyl ether, 1,2-dimethoxyethane and tetrahydrofuran; aromatic hydrocarbons, such as benzene, toluene and xylene; and aliphatic hydrocarbons, such as hexane and octane.

The formylation reaction according to the 1st stage of both process variants is carried out in the presence of a strong base. All the organic and inorganic bases which can usually be employed may be used here. Alkali metal alcoholates, such as sodium methylate, potassium ethylate, lithium propylate and potassium tert.-butylate, are preferably used.

Possible acids which can be employed in carrying out the first stage of process variants (a) and (b) for acidifying the reaction mixture are all the acids customary for such purposes. Hydrochloric acid can preferably be used.

The meaning of the substituent R$^{10}$ in the compounds of the formula (III) varies depending on the base used in carrying out the first stage of the process according to the invention in variants (a) and (b) and depending on whether the reaction mixture has been acidified in the first stage. If alkali metal alcoholates are used as the bases, compounds of the formula (III) in which R$^{10}$ represents an alkali metal, such as, for example, lithium, sodium or potassium, result. If the reaction mixture is acidified, enol-ketones of the formula (III) in which R$^{10}$ represents hydrogen are formed.

The reaction temperatures can be varied within a substantial range in carrying out the process according to the invention both in variant (a) and in variant (b). In general, the 1st stage of both process variants is carried out between $-25°$ and $+60°$ C., preferably between $-10°$ and $+40°$ C.;

the 2nd stage of process variant (a) is carried out between $-25°$ and $+50°$ C., preferably between $-10°$ and $+10°$ C.;

the 3rd stage of process variant (a) and the 2nd stage of process variant (b) are likewise carried out between $-25°$ and $+50°$ C., preferably between $-10°$ and $+10°$ C.;

the reaction with formamidine according to the 3rd stage of process variant (b) is carried out between $-20°$ and $+30°$ C., preferably between $-10°$ and $+10°$ C.; and the cyclization by heat in the last stage of both process variants is carried out between $0°$ and $+100°$ C., preferably between $+50°$ and $+100°$ C..

In carrying out the process according to the invention, equimolar amounts or a slight excess, preferably up to 1.5 moles, of formylating agent, amino-formylating agent and formamidine are preferably employed per mole of methyl ketone of the formula (II) both in variant (a) and in variant (b). Working up and isolation of the compounds of the formula (I) and, if appropriate, also of the individual intermediates of the formulae (III), (IV), (V) and (VI) are carried out by customary methods.

As already mentioned, the 5-acylpyrimidines of the formula (I) are interesting intermediates for the synthesis of substances with a plant growth-regulating and fungicidal activity. Thus, benzyl pyrimidinyl-alkyl ethers of the formula

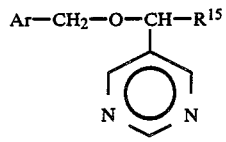
(X)

in which
Ar represents optionally substituted phenyl and
$R^{15}$ represents alkyl, optionally substituted cycloalkyl or optionally substituted phenyl,
are obtained by a process in which 5-acylpyrimidines of the formula

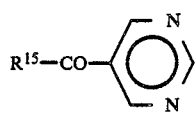
(Ib)

in which $R^{15}$ has the abovementioned meaning, are reduced in the customary manner and the pyrimidinyl-carbinols thus obtained, of the formula

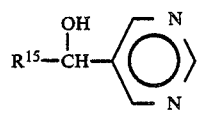
(XI)

in which $R^{15}$ has the abovementioned meaning, are reacted with benzyl halides of the formula Ar—CH₂—Hal    (XII)

in which
Ar has the abovementioned meaning and
Hal represents halogen,
in the presence of a solvent and, if appropriate, in the presence of a strong base (See U.S. Pat. No. 4,436,907 issued Mar. 13, 1984.)

The process according to the invention is illustrated by the following examples.

PREPARATION EXAMPLES

Example 1

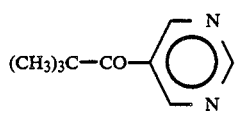
(I-1)

Process variant (a) with isolation of the intermediate of the formula (III-1)

1st stage

(III-1)

56.0 g (0.5 mole) of potassium tert.-butylate are added to a mixture of 50.0 g (0.5 mole) of pinacolone and 42.0 g (0.5 mole) of methyl formate at 15° to 20° C., with cooling. The reaction mixture is subsequently stirred at 30° C. for 12 hours. For working up, 400 ml of diethyl ether are added and the product precipitated is filtered off with suction and dried. 62.3 g (75% of theory) of 4,4-dimethyl-1-hydroxy-1-penten-3-one, as the potassium salt, are obtained in the form of a light yellow powder.

2nd to 4th stage

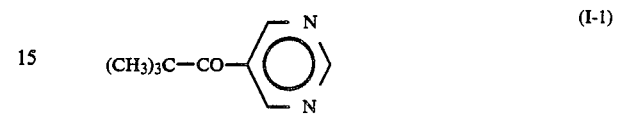
(I-1)

132.1 g (1.27 moles) of formamidine acetate in 800 ml of tetrahydrofuran are added in portions to 166.2 g (1 mole) of the potassium salt of 4,4-dimethyl-1-hydroxy-1-penten-3-one (compare 1st stage) in 800 ml of tetrahydrofuran at 0° C. The reaction mixture is subsequently stirred at 0° C. for 15 minutes, and 165.4 g (1.39 moles) of N,N-dimethylformamide dimethyl acetal are then added. The mixture is subsequently stirred at 0° C. for 1 hour and at 50° to 55° C. for 6 hours. For working up, it is cooled, the potassium acetate is filtered off with suction and the filtrate is subjected to fractional distillation. 49.2 g (30% of theory) of tert.-butyl 5-pyrimidinyl ketone of boiling point $bp_{16}=102°-105°$ C. are obtained.

Example 2

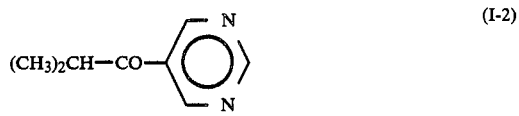
(I-2)

Process variant (a) with isolation of the intermediate of the formula (III-2)

1st stage

(III-2)

344 g (4 moles) of isopropyl methyl ketone are first added dropwise to 216 g (4 moles) of sodium methylate in 1.5 l of diethyl ether at 25° C., and 296 g (4 moles) of ethyl formate are then added dropwise at 30°–35° C. The reaction mixture is subsequently stirred at 25° C. for six hours and the sodium salt precipitated is then filtered off with suction. 360 g (66% of theory) of 1-hydroxy-4-methyl-1-penten-3-one, as the sodium salt, are obtained.

2nd to 4th stage

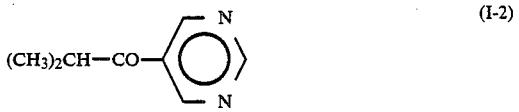
(I-2)

240 g (2.308) moles of formamidine acetate in 1.5 l of tetrahydrofuran are added in portions to 250 g (1.84 moles) of the sodium salt of 1-hydroxy-4-methyl-1-penten-3-one (compare 1st stage) in 1.5 l of tetrahydrofuran at 0° C. The reaction mixture is subsequently stirred at 0° C. for 15 minutes, and 298 g (2.5 moles) of N,N-dimethylformamide dimethyl acetal are then added. The reaction mixture is subsequently stirred at 0° C. for 1 hour and at 50°-55° C. for six hours. For working up, the mixture is cooled and the sodium acetate is filtered off with suction. The filtrate is subjected to fractional distillation. 91.6 g (33.2% of theory) of isopropyl 5-pyrimidinyl ketone of boiling point $bp_{18} = 112°-115°$ obtained.

Example 3

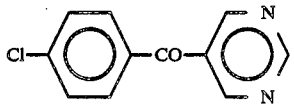 (I-3)

Process variant (b) with isolation of the intermediate of the formula (III-3)

1st stage

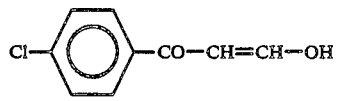 (III-3)

300 g (1.94 moles) of 4-chloroacetophenone are added dropwise to a suspension of 105 g (1.94 moles) of sodium methylate in 1.7 l of diethyl ether. 144 g (1.94 moles) of ethyl formate are added dropwise at room temperature, with cooling. The reaction mixture is stirred under reflux for 3 hours and cooled to room temperature and the precipitate is filtered off with suction. The precipitate is dissolved in water, the pH value is brought to 1-2 with dilute hydrochloric acid, the mixture is extracted with ethyl acetate and the organic phase is concentrated. 216 g (61% of theory) of 4-chlorophenyl hydroxyvinyl ketone of melting point 44° C. are obtained.

2nd and 3rd stage

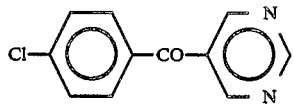 (I-3)

7.7 g (0.065 mole) of N,N-dimethylformamide dimethyl acetal are added in portions to 10 g (0.055 mole) of 4-chlorophenyl hydroxyvinyl ketone (compare 1st stage) in 10 ml of toluene at 0° C. The reaction mixture is subsequently stirred for 15 minutes, and 5.7 g (0.055 mole) of formamidine acetate are then added. After further subsequent stirring for 15 minutes, a solution of 3 g (0.055 mole) of sodium methylate in 80 ml of ethanol is added dropwise and the mixture is subsequently stirred under reflux for 8 hours. The reaction mixture is allowed to cool and is poured onto 400 ml of water and extracted with toluene. The organic phase is washed with water, dried over sodium sulphate and concentrated. The residue is purified by column chromatography (ethyl acetate: cyclohexane =3:1; silica gel). 3.7 g (31% of theory) of 4-chlorophenyl 5-pyrimidinyl ketone of melting point 110°-112° C. are obtained.

The following 5-acylpyrimidines of the formula (I)

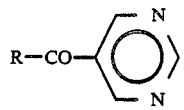 (I)

can be obtained analogously and in accordance with the process conditions described:

| Example No. | R | Physical constants |
|---|---|---|
| 4 | Cl—⟨⟩—O—C(CH$_3$)$_2$— | Melting point: 106° C. |
| 5 | F—⟨⟩—CH$_2$—C(CH$_3$)$_2$— | $n_D^{20} = 1.5473$ |
| 6 | Cl,Cl—⟨⟩—O—CH$_2$—C(CH$_3$)$_2$— | Melting point: 178° C. |
| 7 | Cl—⟨⟩—S—CH$_2$—C(CH$_3$)$_2$— | Melting point: 58° C. |
| 8 | CH$_3$OCH$_2$—C(CH$_3$)$_2$— | $n_D^{20} = 1.4964$ |
| 9 | Cl-⟨⟩— | Melting point: 62° C. |
| 10 | Cl,Cl-⟨⟩— | Melting point: 64° C. |
| 11 | Cl,Cl-⟨⟩— | Melting point: 95° C. |
| 12 | CF$_3$-⟨⟩— | Melting point: 90-92° C. |

Preparation of benzyl pyrimidinyl-alkyl ethers of the formula (X)

Example (X-1)

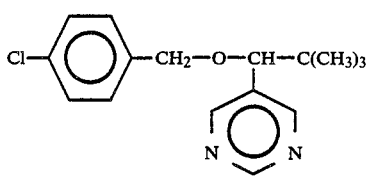 (X-1)

Preparation of the starting substance

HO—HC—C(CH$_3$)$_3$

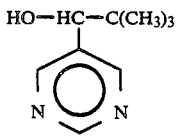 (XI-1)

1.27 g (0.034 mole) of sodium borohydride in 10 ml of water are added to 16.4 g (0.1 mole) of tert.-butyl 5-pyrimidinyl ketone in 100 ml of methanol at room temperature. The reaction mixture is stirred at room temperature for 1 hour and concentrated in vacuo, the residue is distilled in methylene chloride and the solution is concentrated again in vacuo. 15.8 g (95% of theory) of 5-(1-hydroxy-2,2-dimethyl-propyl)-pyrimidine of melting point 93°-95° C. are obtained.

Preparation of the end product

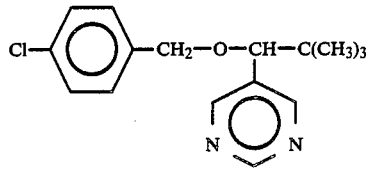
(X-1)

200 ml of 33% strength aqueous sodium hydroxide solution are added to a solution of 16.6 g of 5-(1-hydroxy-2,2-dimethyl-propyl)-pyrimidine, 32.2 g of 4-chlorobenzyl chloride and 6 g of tetrabutylammonium bromide in 200 ml of toluene. The reaction mixture is stirred vigorously at room temperature for 18 hours.

The aqueous phase is separated off and the organic phase is diluted with toluene, washed four times with water and once with saturated aqueous sodium chloride solution, dried over sodium sulphate and concentrated. The oily residue is dissolved in ether/hexane and the solution is gassed with hydrogen chloride. The crystalline precipitate formed is filtered off with suction and rinsed with ether, and ethyl acetate/1N aqueous sodium hydroxide solution is added, whereupon the free base is formed again.

After recrystallization from hexane, 20.3 g (70% of theory) of 5-[1-(4-chlorobenzyloxy)-2,2-dimethyl-propyl]-pyrimidine of melting point 77°-78.5° C. are obtained.

Example (X-2)

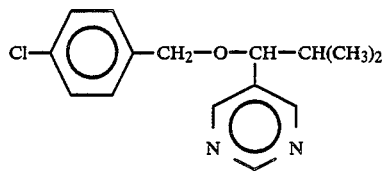
(X-2)

Preparation of the starting substance

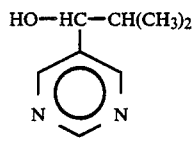
(XI-2)

1.27 g (0.034 mole) of sodium borohydride in 10 ml of water are added to 15 g (0.1 mole) of isopropyl 5-pyrimidinyl ketone in 100 ml of methanol at room temperature. The reaction mixture is subsequently stirred at room temperature for 1 hour and is concentrated in vacuo, the residue is taken up in methylene chloride and the mixture is concentrated again in vacuo. 15.1 g (99.3% of theory) of 5-(1-hydroxy-2-methyl-propyl)-pyrimidine of refractive index $n_D^{20} = 1.5082$ are obtained.

Preparation of the end product

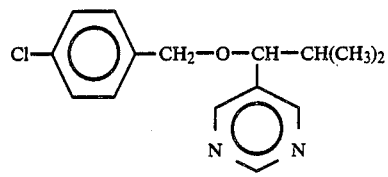
(X-2)

100 ml of 33% strength aqueous sodium hydroxide solution are added to a solution of 6.8 g of 5-(1-hydroxy-2-methyl-propyl)-pyrimidine, 14.5 g of 4-chlorobenzyl chloride and 3 g of tetrabutylammonium bromide in 100 ml of toluene. The reaction mixture is stirred at room temperature for 2 days.

The aqueous phase is separated off and the organic phase is diluted with toluene, washed four times with water and once with saturated aqueous sodium chloride solution, dried over sodium sulphate and concentrated. The oily residue is dissolved in ether/hexane and the solution is gassed with hydrogen chloride. The crystalline precipitate formed is filtered off with suction and rinsed with ether, and ethyl acetate/1N aqueous sodium hydroxide solution is added, whereupon the free base is formed again.

10.2 g (82% of theory) of 5-[1-(4-chloro-benzyloxy)-2-methylpropyl]-pyrimidine are obtained as a light oil which slowly crystallizes completely (melting point 33°-35° C.).

Comparison Example

Preparation of 5-(1-hydroxy-2,2-dimethyl-propyl)-pyrimidine of the formula (XI-1) by the process known hitherto

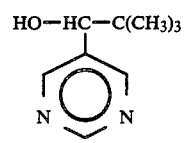
(XI-1)

225 g of 5-bromopyrimidine are dissolved in 1.5 l of absolute tetrahydrofuran/1,000 ml of absolute ether and the solution is cooled to −120° C. 250 ml of 50% strength n-butyl-lithium (in n-hexane) are added dropwise at an internal temperature of −105° to −115° C. in the course of 2 hours. The mixture is subsequently stirred at this temperature for 1 hour. 309 ml of trimethylacetaldehyde are then added dropwise in the course of 2 hours. The reaction mixture is then subsequently stirred at this temperature for 4 hours. It is allowed to warm to room temperature overnight and 83 g of ammonium chloride, dissolved in a minimum amount of water, are then added. The aqueous phase is separated off and the organic phase is washed twice with saturated sodium chloride solution, dried over sodium sulphate and concentrated. After recrystallization of the residue from acetonitrile, 155 g (66% of theory) of 5-(1-hydroxy-2,2-dimethylpropyl)pyrimidine of melting point 94°-96° C. are obtained.

It is understood that the specification and examples are illustrative but not limitative of the present inven-

We claim:

1. A process for the preparation of a 5-acylpyrimidine of the formula

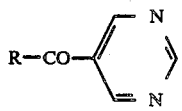

in which

R represents straight-chain or branched alkyl with 1 to 12 carbon atoms, straight-chain or branched alkenyl with 3 to 6 carbon atoms, straight-chain or branched alkinyl with 3 to 6 carbon atoms or cycloalkyl and cycloalkylalkyl with in each case 3 to 7 carbon atoms in the alkyl part and in each case optionally mon-, di- or tri-substituted by identical or different alkyl substituents with 1 to 4 carbon atoms; or represents phenyl which is optionally mono-, di- or tri-substituted by identical or different substituents selected from the group consisting of halogen, hydroxyl, alkyl, alkoxy and alkylthio with in each case 1 to 4 carbon atoms; halogenoalkyl, halognoalkoxy and halogenoalkylthio with in each case 1 to 4 carbon atoms and 1 to 5 identical or different halogen atoms; nitro, cyano and alkoxycarbonyl with 1 to 4 carbon atoms in the alkoxy part, and phenyl and phenoxy, in each case optionally substituted by halogen; or furthermore represents 5- to 6-membered heteroaryl which has 1 to 3 oxygen, nitrogen and/or sulphur atoms, and is optionally mono-, di or tri-substituted by identical or different substituents, possible substituents being the abovementioned substituents on phenyl, or represents the groupings

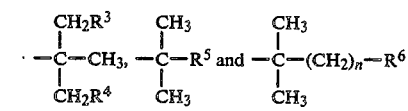

wherein $R^3$ represents fluorine, chlorine or bromine;

$R^4$ represents hydrogen, fluorine, chlorine or bromine;

$R^5$ represents straight-chain or branched alkenyl with 2 to 4 carbon atoms, straight-chain or branched alkinyl with 3 to 5 carbon atoms, or the CHO group, alkoximinomethyl with 1 to 4 carbon atoms in each alkoxy part, dialkoxymethyl with 1 to 4 carbon atoms in each alkoxy part, dioxolanyl and dioxanyl;

$R^6$ represents cyano, or represents phenyl which is optionally mono- di or tri-substituted by identical or different substituents, possible substituents being the substituents on phenyl which have already been mentioned above, or represents the groupings $-XR^7$ and $-CONR^8R^9$, wherein $R^7$ represents straight-chain or branched alkyl with 1 to 6 carbon atoms or halogenoalkyl with 1 to 4 carbon atoms and 1 to 5 identical or different halogen atoms or represents phenyl or phenylalkyl, with 1 or 2 carbon atoms in the alkyl part, each of which is optionally mono-, di- or tri-substituted by identical or different substituents, possible substituents in each case being the substituents on phenyl which have already been mentioned above;

$R^8$ represents hydrogen or straight-chain or branched alkyl with 1 to 4 carbon atoms, or represents phenyl which is optionally mono- di- or tri-substituted by identical or different substituents, possible substituents being the substituents on phenyl which have already been mentioned above;

$R^9$ represents hydrogen or straight-chain or branched alkyl with 1 to 4 carbon atoms;

x represents oxygen or sulphur and n represents the number 0, 1 or 2, comprising reacting a methyl ketone of the formula $$R-CO-CH_3$$

(a) in a first stage with a formylating reagent selected from the group consisting of a formic acid alkyl ester with 1 to 4 carbon atoms in the alkyl group, and phenyl formate, in the presence of a base at a temperature between $-25°$ C. and $+60°$ C., thereby forming an enol-ketone of the formula

in which $R^{10}$ represents hydrogen or an alkali metal, in a second stage reacting the enol-lactone with formamidine or a salt thereof with an organic or inorganic acid, at a temperature between $-25°$ C. and $+50°$ C. thereby to form a formamidine derivative of the formula

in a third state reacting the formamidine derivative with an amino-formylating agent selected from the group consisting of (α) a formamidine acetal of the formula

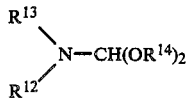

in which $R^{12}$ and $R^{13}$ independently of one another represent metyl, ethyl, n-propyl, isopropyl or n-butyl, or $R^{12}$ and $R^{13}$, together With the nitrogen atom to which they are bonded, represent pyrrolidinyl, piperidinyl, morpholinyl or N-methyl-piperazinyl, and $R^{14}$ represents methyl, ethyl or n-propyl, (β) an aminal ester of the formula

and (γ) a formimimum halide of the formula

in which

Hal represents halogen, at a temperature between −25° C. and +50° C., thereby to form a compound of the formula

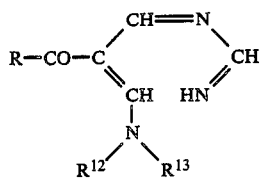

and, in a fourth stage cyclizing such compound by heating to a temperature between 0° C. and 100° C., or (b) in a first stage with a formylating reagent selected from the group consisting of a formic acid alkyl ester with 1 to 4 carbon atoms in the alkyl group, and phenyl formate, in the presence of a base at a temperature between −25° C. and +60° C., to form an enol-ketone of the formula

in a second stage reacting the enol-lactone with an amino-formylating agent selected from the group consisting of (α) a formamidine acetal of the formula

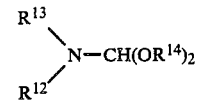

(β) an amimal ester of the formula

and (γ) a formiminum halide of the formula

at a temperature between −25° C. and +50° C., to form a compound of the formula

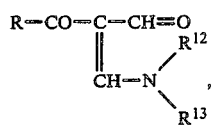

reacting such compound with formamidine at a temperature between −20° C. and +30° C., and then cyclizing the product formed by heating to a temperature between 0° C. and 100° C.

2. A process according to claim 1, wherein successive steps are effected without isolation of the preceding product.

3. The process according to claim 1, wherein the base is an alkali metal alcoholate.

* * * * *